United States Patent
Flohr et al.

(10) Patent No.: US 7,368,446 B2
(45) Date of Patent: May 6, 2008

(54) 4-HYDROXY-4-METHYL-PIPERIDINE-1-CARBOXYLIC ACID (4-METHOXY-7-MORPHOLIN-4-YL-BENZOTHIAZOL-2-YL)-AMIDE

(75) Inventors: Alexander Flohr, Reinach (CH); Jean-Luc Moreau, Lutterbach (FR); Sonia Maria Poli, Onex-Geneve (CH); Claus Riemer, Freiburg (DE); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 126 days.

(21) Appl. No.: 11/132,019

(22) Filed: May 18, 2005

(65) Prior Publication Data

US 2005/0261289 A1 Nov. 24, 2005

(30) Foreign Application Priority Data

May 24, 2004 (EP) ................... 04102262

(51) Int. Cl.
*A61K 31/535* (2006.01)
*C07D 413/14* (2006.01)

(52) U.S. Cl. ................... 514/233.8; 544/130
(58) Field of Classification Search ................ 544/130; 514/233.8
See application file for complete search history.

(56) References Cited

U.S. PATENT DOCUMENTS

| 3,725,428 | A | 4/1973 | Janiak |
| 4,028,374 | A | 6/1977 | Pelosi, Jr. et al. |
| 5,099,021 | A | 3/1992 | Worther et al. |
| 6,878,720 | B2 | 9/2005 | Altmann et al. |

FOREIGN PATENT DOCUMENTS

| DE | 1 953 149 | | 5/1970 |
| EP | 0 199 400 | A | 10/1986 |
| EP | 295 656 | | 12/1988 |
| EP | 0343893 | | 11/1989 |
| EP | 0404440 | A | 12/1990 |
| EP | 427 963 | | 5/1991 |
| EP | 0604657 | | 7/1994 |
| FR | 2 753 970 | A | 4/1998 |
| GB | 1 345 552 | A | 1/1974 |
| GB | 1 538 822 | A | 1/1979 |
| WO | WO 99/37630 | | 1/1990 |
| WO | WO 99/24035 | | 5/1999 |
| WO | WO 00/18767 | | 4/2000 |
| WO | WO 00/27819 | A | 5/2000 |
| WO | WO 01/19360 | A2 | 9/2000 |
| WO | WO 01/87786 | | 12/2001 |
| WO | WO 03/049741 | | 6/2003 |
| WO | WO 03/053946 | | 7/2003 |

OTHER PUBLICATIONS

Poulsen, et al., Bioorganic & Medicinal Chemistry, vol. 6 (1998) pp. 619-641.
Müller, et al., Bioorganic & Medicinal Chemistry, vol. 6, (1998) pp. 707-719.
Kim, et al., J. Med. Chem., (1998), vol. 41, pp. 2835-2845.
Li, et al., J. Med. Chem., (1998), vol. 41, pp. 3186-3201.
Baraldi, et al., J. Med. Chem., (1998), vol. 41, pp. 2126-2133.
Li, et al., J. Med. Chem., (1999), vol. 42, pp. 706-721.
Baraldi, et al., J. Med. Chem., (1996), vol. 39, pp. 1164-1171.
Colotta, et al., Arch. Pharm. Med. Chem., vol. 332, pp. 39-41 (1999).
Auchampach, et al., Am. J. Physiol. vol. 276, H1113-1116 (1999).
Naunyn-Schmiedeberg, Arch. Pharmacol. vol. 362, pp. 375-381 (2000).
Patent Abstracts of Japan, vol. 1999, No. 10, JP 11 130761a.
Pandeya, S. N. et al:, Indian Drugs (1985), 23(3), 146-51 XP0080000199.
Daidone, G. et al., vol. 44, No. 5 (1989), pp. 465-473, XP001053114.
The Merck Index 12th Ed. (1996) p. 506.
Abstract corresponding to FR 2 753 970 (B6), 1998.

*Primary Examiner*—Rebecca Anderson
(74) *Attorney, Agent, or Firm*—George W. Johnston; Patricia S. Rocha-Tramaloni; Kimberly J. Prior

(57) ABSTRACT

The present invention relates to the compound of formula

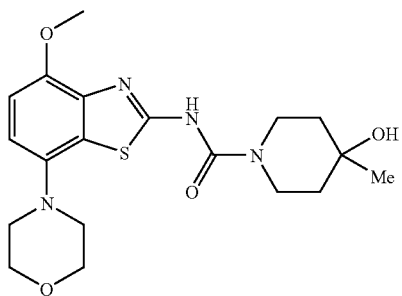

which is 4-hydroxy-4-methyl-piperidine-1-carboxylic acid (4-methoxy-7-morpholin-4-yl-benzothiazol-2-yl)-amide, and to pharmaceutically acceptable acid addition salts thereof. It has been found that the compound is useful for the treatment or prevention of Alzheimer's disease, Parkinson's disease, Huntington's disease, neuroprotection, schizophrenia, anxiety, pain, respiration deficits, depression, ADHD (attention deficit hyper-activity disorder), drug addiction to amphetamines, cocaine, opioids, ethanol, nicotine, or cannabinoids, or for the treatment of asthma, allergic responses, hypoxia, ischemia, seizure, substance abuse, or for use as muscle relaxants, antipsychotics, antiepileptics, anticonvulsants and cardioprotective agents.

9 Claims, No Drawings

4-HYDROXY-4-METHYL-PIPERIDINE-1-CARBOXYLIC ACID (4-METHOXY-7-MORPHOLIN-4-YL-BENZOTHIAZOL-2-YL)-AMIDE

FIELD OF THE INVENTION

The present invention relates to 4-hydroxy-4-methyl-piperidine-1-carboxylic acid(4-methoxy-7-morpholin-4-yl-benzothiazol-2-yl)-amide, which is a compound of formula I

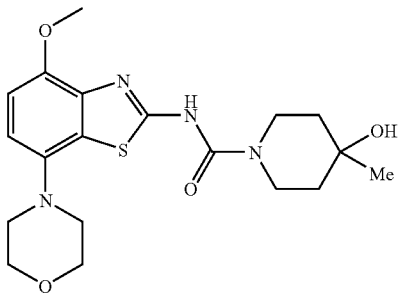

and to pharmaceutically acceptable acid addition salts thereof. This compound is generically encompassed by WO 01/097786. The invention also relates to use of this compound as a selective adenosine $A_{2A}$ receptor antagonist.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The adenosine receptors have been classified as $A_1$, $A_{2A}$, $A_{2B}$ and $A_3$ receptors, belonging to the family of G protein-coupled receptors. Activation of aderosine receptors by adenosine initiates signal transduction mechanisms. These mechanisms are dependent on the receptor associated G protein. Each of the adenosine receptor subtypes has been classically characterized by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system activates phospholipase C and modulates both potassium and calcium ion channels. The $A_3$ subtype, in addition to its association with adenylate cyclase, also stimulates phospholipase C and activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse and shows 45% homology with the human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neurotransmitter able to modulate many aspects of physiological brain function. Endogenous adenosine, a central link between energy metabolism and neuronal activity, varies according to behavioral state and (patho)physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischemia and seizures. These neurotransmitters are ultimately responsible for neural degeneration and neural death, which causes brain damage or death of the individual. The adenosine $A_1$ agonists mimic the central inhibitory effects of adenosine and may therefore be useful as neuroprotective agents. Adenosine has been proposed as an endogenous anticonvulsant agent, inhibiting glutamate release from excitatory neurons and inhibiting neuronal firing. Adenosine agonists therefore may be used as antiepileptic agents. Furthermore, adenosine antagonists have proven to be effective as cognition enhancers. Selective $A_{2A}$ antagonists have therapeutic potential in the treatment of various forms of dementia, for example in Alzheimer's disease, and of neurodegenerative disorders, e.g. stroke. Adenosine $A_{2A}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, and cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2A}$ receptors on adrenergic function may have implications for a variety of disorders such as coronary artery disease and heart failure. $A_{2A}$ antagonists may be of therapeutic benefit in situations in which an enhanced anti-adrenergic response is desirable, such as during acute myocardial ischemia. Selective antagonists at $A_{2A}$ Areceptors may also enhance the effectiveness of adenosine in terminating supraventricula arrhytmias.

Adenosine modulates many aspects of renal function, including renin release, glomerular filtration rate and renal blood flow. Compounds which antagonize the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:

Bioorganic & Medicinal Chemistry, 6, (1998), 619-641,
Bioorganic & Medicinal Chemistry, 6, (1998), 707-719,
J. Med. Chem., (1998), 41, 2835-2845,
J. Med. Chem., (1998), 41, 3186-3201,
J. Med. Chem., (1998), 41, 2126-2133,
J. Med. Chem., (1999), 42, 706-721,
J. Med. Chem., (1996), 39, 1164-1171,
Arch. Pharm. Med. Chem., 332, 39-41, (1999),
Am. J. Physiol., 276, H1113-1116, (1999) or
Naunyn Schmied, Arch. Pharmacol. 362, 375-381, (2000).

SUMMARY OF THE INVENTION

The present invention provides the compound 4-hydroxy-4-methyl-piperidine-1-carboxylic acid(4-methoxy-7-morpholin-4-yl-benzothiazol-2-yl)-amide, which has the formula

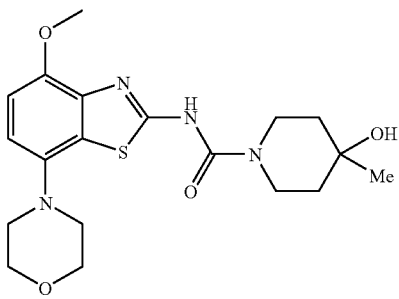

I and to pharmaceutically acceptable acid addition salts thereof The present invention further provides methods for preparation of such compounds.

Surprisingly, it has been found that the compound of formula I is a high affinity, highly selective adenosine $A_{2A}$ receptor antagonist with potent and long-acting in vivo oral antagonism of adenosine $A_{2A}$ receptor agonist-induced behavior. Thus, the invention provides pharmaceutical compositions comprising a therapeutically effective amount of the compound of formula I. The invention also provides methods for the treatment of diseases related to modulation of the adenosine system. For example, the invention provides methods for the treatment of Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, or cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents for disorders such as coronary artery disease and heart failure. The most preferred indications in accordance with the present invention are those which are based on the $A_{2A}$ receptor antagonistic activity and which include disorders of the central nervous system, for example the treatment or prevention of Alzheimer's disease, depressive disorders, drug addiction, neuroprotection, Parkinson's disease and ADHD.

DETAILED DESCRIPTION OF THE INVENTION

The following definitions of general terms used herein apply irrespective of whether the terms in question appear alone or in combination. It must be noted that, as used in the specification and the appended claims, the singular forms "a," "an," and "the" include plural forms unless the context clearly dictates otherwise.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "pharmaceutically acceptable" such as pharmaceutically acceptable carrier, excipient, etc. means pharmacologically acceptable and substantially non-toxic to the subject to which the particular compound is administered.

The term "therapeutically effective amount" means an amount that is effective to prevent, alleviate, or ameliorate symptoms of disease or prolong the survival of the subject being treated.

The present invention provides the compound 4-hydroxy-4-methyl-piperidine-1-carboxylic acid(4-methoxy-7-morpholin-4-yl-benzothiazol-2-yl)-amide, which has the formula

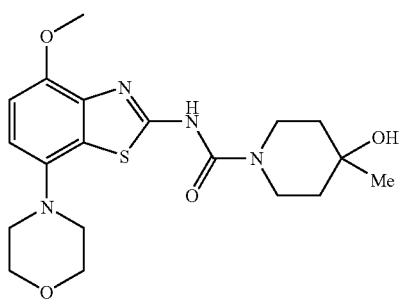

I and pharmaceutically acceptable acid addition salts thereof

The present compound of formula I and its pharmaceutically acceptable salts can be prepared by methods known in the art, for example, by processes described below, which processes comprise a) reacting the compound of formula

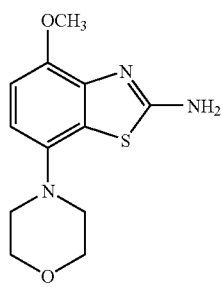

II with the compound of formula

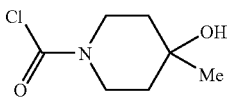

III to produce a compound of formula

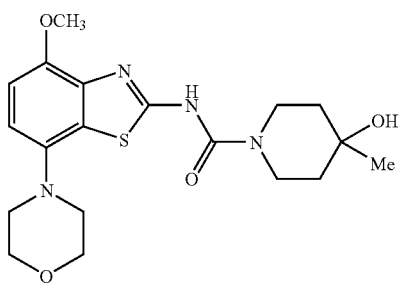

I or b) reacting a compound of formula

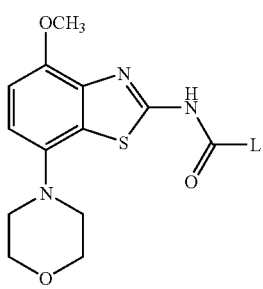

IV with the compound of formula

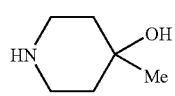

V to produce a compound of formula

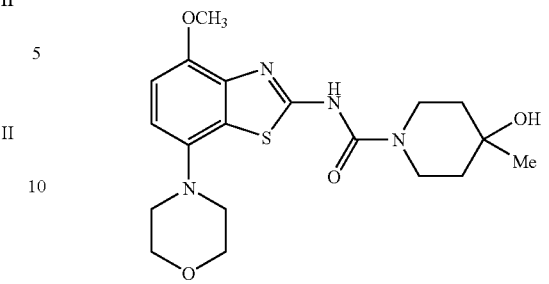

I wherein L is a leaving group such as halogen, —O-phenyl, —O-nitro-phenyl or —O-lower alkyl, and if desired, converting the compounds obtained into pharmaceutically acceptable acid addition salts.

The compounds of formula I may be prepared in accordance with process variants a) and b).

Furthermore, in examples 1-7 and in the following schemes 1, 2 and 3, the preparation of a compound of formula I is described in more detail.

The starting materials are known compounds or may be prepared according to methods known in the art.

Preparation of Compounds of Formula I

One method of preparation of the compound of formula (I) is in accordance with the following scheme 1. To a solution of the intermediate 7-(morpholin-4-yl)-4-methoxy-benzothiazol-2-ylamine (II), which may be prepared according to scheme 3, in dichloromethane is subsequently added a base, e.g. pyridine or diisopropyl-ethylamine, and the compound of formula (III), and the resulting solution is stirred for about 45 minutes at ambient temperature. Saturated aqueous sodium hydrogen carbonate is added, and the organic phase is separated and dried.

Scheme 1

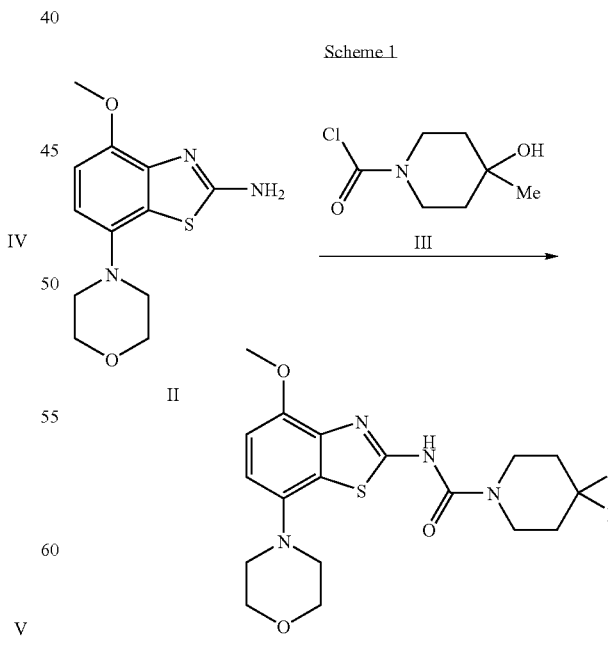

Another method for preparing the compound of formula (I) employs the compound of formula (IV) and is depicted in scheme 2. The compound of formula (IV) can be prepared according to methods well known in the art, for example, the methods described in WO01/97786. A base, e.g. pyridine or diisopropyl-ethylamine and a compound of formula (V) are added to a solution of the compound of formula (IV) in an inert solvent, e.g. dichloromethane, and the resulting solution is stirred for about 45 minutes at 45° C. After cooling to ambient temperature, saturated aqueous sodium hydrogen carbonate is added, the organic phase is separated and dried.

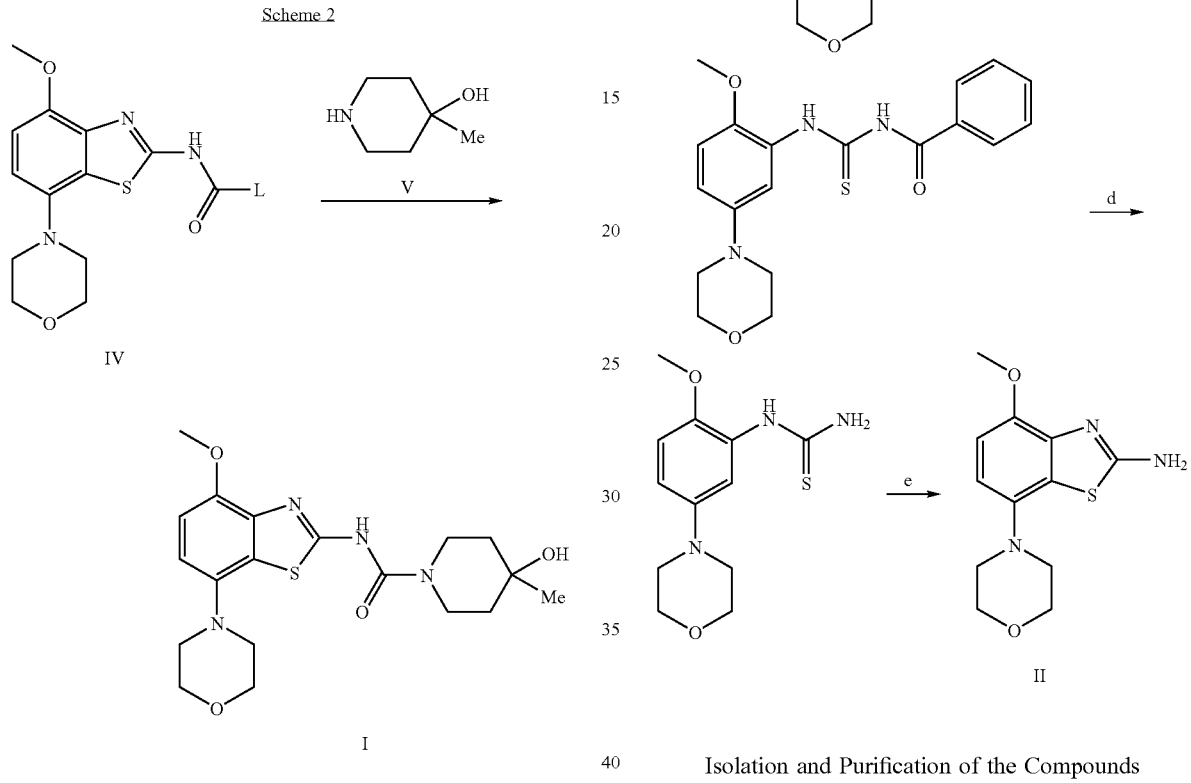

wherein L is a leaving group, such as halogen, —O-phenyl, —O-nitro-phenyl or O-lower alkyl.

Yet another method of preparation of the compound of formula I is scheme 3, as follows where
a is morpholine, Pd(Ac)$_2$, 2-biphenyl-dicyclohexyl phosphine, K$_3$PO$_4$, DME;
b is H$_2$, Pd on carbon, methanol;
c is benzoyl isothiocyanate, acetone;
d is methanolic sodium methanolate; and
e is bromine in trichloromethane.

Scheme 3

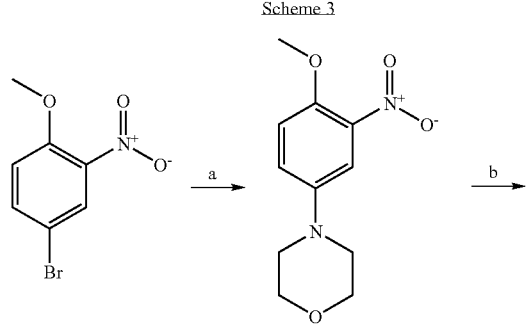

Isolation and Purification of the Compounds

Isolation and purification of the compound and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be obtained by reference to the preparations and examples herein below. However, other equivalent separation or isolation procedures could of course also be used.

Salts of Compounds of Formula I

The conversion of the compound of formula I to a corresponding acid addition salt is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of Formula I may be converted to the corresponding free bases by treatment with at least a stoichiometric equivalent of a suitable base such as sodium or potassium hydroxide, potassium carbonate, sodium bicarbonate, ammonia, and the like.

The compound of formula I and its pharmaceutically usable addition salts possess valuable pharmacological properties. Specifically, it has been found that the compound of the present invention is an adenosine receptor ligand and possesses a high affinity towards the adenosine $A_{2A}$ receptor.

The compounds were investigated in accordance with the tests given hereinafter.

Test Description

The affinity of 4-hydroxy-4-methyl-piperidine-1-carboxylic acid(4-methoxy-7-morpholin-4-yl-benzothiazol-2-yl)-amide for the $A_{2A}$ receptor was evaluated at human $A_{2A}$ receptors recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM $CaCl_2$ and 10 mM $MgCl_2$ (pH 7.4) (buffer A). The $^3$H SCH-58261 (Dionisotti et al., 1997, Br J Pharmacol 121, 353; 1 nM) binding assay was carried out in 96-well-plates in the presence of approximately 2.5 µg of membrane protein, 0.5 mg of Ysi-poly-1-lysine SPA beads and 0.1 U adenosine deaminase in a final volume of 200 µl of buffer. Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

Test Results

4-Hydroxy-4-methyl-piperidine-1-carboxylic acid(4-methoxy-7-morpholin-4-yl-benzothiazol-2-yl)-amide was found to be a high affinity, potent and selective antagonist at recombinant human adenosine $A_{2A}$ receptors. It has an affinity (pKi) of 8.3 for the human $A_{2A}$ receptor with over 2 orders of magnitude of selectivity for the $A_{2A}$ receptor compared to $A_1$, $A_{2B}$ and $A_3$ receptors. Further studies assessed the selectivity of 4-hydroxy-4-methyl-piperidine-1-carboxylic acid(4-methoxy-7-morpholin-4-yl-benzothiazol-2-yl)-amide versus a variety of neurotransmitter transporters, ion channels, and enzyme targets. 4-Hydroxy-4-methyl-piperidine-1-carboxylic acid(4-methoxy-7-morpholin-4-yl-benzothiazol-2-yl)-amide exhibited more than 1000-fold selectivity for the $A_{2A}$ receptor over the targets tested.

The activity in vitro was evaluated by studying the ability of the compound to antagonize the NECA-stimulated (a non-specific adenosine receptor agonist) $Ca^{2+}$ flux in CHO cells expressing human $A_{2A}$ receptors coupled to the G protein Gα16. 4-Hydroxy-4-methyl-piperidine-1-carboxylic acid(4-methoxy-7-morpholin-4-yl-benzothiazol-2-yl)-amide inhibited $A_{2A}$-mediated responses with a $pIC_{50}$ of 8.83 (Hill slope 0.6). 4-Hydroxy-4-methyl-piperidine-1-carboxylic acid(4-methoxy-7-morpholin-4-yl-benzothiazol-2-yl)-amide antagonized the NECA-stimulated $Ca^{2+}$ flux in CHO cells expressing human $A_1$ receptors coupled to the G protein Gα16 with a pIC50 of 5.22 (Hill slope 0.7). Thus, in this functional assay, 4-hydroxy-4-methyl-piperidine-1-carboxylic acid(4-methoxy-7-morpholin-4-yl-benzothiazol-2-yl)-amide exhibited >4000 fold selectivity for the human $A_{2A}$ receptor over the human $A_1$ receptor. In vivo 4-hydroxy-4-methyl-piperidine-1-carboxylic acid(4-methoxy-7-morpholin-4-yl-benzothiazol-2-yl)-amide was found to be a potent, long-acting, orally-active antagonist. It antagonizes hypolocomotion induced in rats with subcutaneous injections of 0.01 mg/kg of APEC, an adenosine $A_{2A}$ receptor agonist. The dose for this compound calculated to inhibit 50% of the APEC-induced hypolocomotion following oral administration was 0.5 mg/kg. A plasma concentration of 290 ng/ml is required to completely antagonize this APEC-induced hypolocomotion. This antagonism persisted for a number of hours and had a functional half-life of about 8 hours in this model.

The pharmacokinetic parameters have been evaluated in both rats and dogs. In rats, after intravenous dosing, the compound has a half-life of 4 hours, a clearance of 11 ml/min/kg, a volume of distribution of 1.4 l/kg; the oral bioavailability after administration of 5 mg/kg to rats is 77%. In dogs, after intravenous dosing, the molecule has a half-life of 2.2 hours, a clearance of 8 ml/min/kg, a volume of distribution of 1.2 l/kg; the oral bioavailability at 5 mg/kg is 88%. In conclusion, 4-hydroxy-4-methyl-piperidine-1-carboxylic acid(4-methoxy-7-morpholin-4-yl-benzothiazol-2-yl)-amide was found to be a high affinity, highly selective adenosine $A_{2A}$ receptor antagonist with potent and long-acting in vivo oral antagonism of $A_{2A}$ receptor agonist-induced behavior.

The present invention also provides pharmaceutical compositions containing a compound of formula I or a pharmaceutically acceptable salt of the compound of formula I and a pharmaceutically acceptable excipient. Such pharmaceutical compositions can be in the form of tablets, coated tablets, dragées, hard and soft gelatine capsules, solutions, emulsions or suspensions. The pharmaceutical compositions also can be in the form of suppositories, or injectable solutions.

The pharmaceutical compositions of the invention, in addition to the compound of formula I or a pharmaceutically acceptable salt thereof, contain a pharmaceutically acceptable excipient. Suitable pharmaceutically acceptable excipients include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example in the form of injectable solutions.

In accordance with the invention, the compound of formula I as well as its pharmaceutically acceptable salts are useful in the treatment or prevention of illnesses based on adenosine $A_{2A}$ receptor antagonist activity, such as Alzheimer's disease, Parkinson's disease, Huntington's disease, neuroprotection, schizophrenia, anxiety, pain, respiration deficits, depression, ADHD (attention deficit hyper-activity disorder), drug addiction to amphetamines, cocaine, opioids, ethanol, nicotine, or cannabinoids, or for the treatment of asthma, allergic responses, hypoxia, ischemia, seizure, substance abuse, or for use as muscle relaxants, antipsychotics, antiepileptics, anticonvulsants and cardioprotective agents.

Thus, the invention provides a method for the treatment of a disorder selected from the group consisting of Alzheimer's disease; Parkinson's disease; Huntington's disease; neuroprotection; schizophrenia; anxiety; pain; respiration deficits; depression; ADHD (attention deficit hyper-activity disorder); drug addiction to amphetamines, cocaine, opioids, ethanol, nicotine, or cannabinoids; asthma; allergic responses; hypoxia; ischemia; seizure; and substance abuse; which comprises administering to a patient a therapeutically effective amount of a compound of formula I

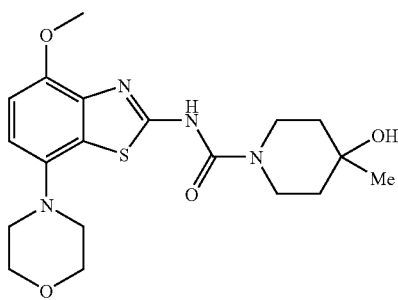

I which is 4-hydroxy-4-methyl-piperidine-1-carboxylic acid (4-methoxy-7-morpholin-4-yl-benzothiazol-2-yl)-amide or a pharmaceutically acceptable salt thereof The most preferred indications in accordance with the present invention are those, which include disorders of the central nervous system, for example the treatment or prevention of Parkinson's disease, ADHD, depressive disorders and drug addiction.

Thus, the present invention provides a method for the treatment of Parkinson's disease which comprises administering to a patient a therapeutically effective amount of the compound of formula I or a pharmaceutically acceptable salt thereof. The invention also provides a method for the treatment of ADHD (attention deficit hyper-activity disorder) which comprises administering to a patient a therapeutically effective amount of the compound of formula I or a pharmaceutically acceptable salt thereof. The invention further provides a method for the treatment of depression which comprises administering to a patient a therapeutically effective amount of the compound of formula I or a pharmaceutically acceptable salt thereof. The present invention provides a method for the treatment of drug addiction to amphetamines, cocaine, opioids, ethanol, nicotine or cannabinoids which comprises administering to a patient a therapeutically effective amount of the compound of formula I or a pharmaceutically acceptable salt thereof.

The dosage at which the compound of formula I or its pharmaceutically acceptable salt can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. In one embodiment, the compound preferably can be administered at a dose from about 0.01 mg to 100 mg, more preferably at a dose from about 0.01 to about 10 mg. In another embodiment, the compound preferably can be administered in an amount from about 10 mg to 1000 mg, more preferably at a dose from about 100 mg to 1000 mg. In another embodiment, the compound preferably can be administered in an amount from about 200 mg to 800 mg, more preferably about 400 mg to 600 mg. In yet another embodiment, the compound preferably can be administered in an amount from about 10 mg to about 200 mg, more preferably about 50 mg to 100 mg. The daily dosage may be administered as single dose or in divided doses and, in addition, the upper limit can also be exceeded when this is found to be indicated.

The following preparation and examples illustrate the invention but are not intended to limit its scope.

EXAMPLE 1

4-Hydroxy-4-methyl-piperidine-1-carboxylic acid(4-methoxy-7-morpholin-4-yl-benzothiazol-2-yl)-amide (I)

To a solution of (4-methoxy-7-morpholin-4-yl-benzothiazol-2-yl)-carbamic acid phenyl ester (3.2 g, 8.3 mmol) and N-ethyl-diisopropyl-amine (4.4 ml, 25 mmol) in trichloromethane (50 ml) is added a solution of 4-hydroxy-4-methyl-piperidine in trichloromethane (3 ml) and tetrahydrofurane (3 ml) and the resulting mixture heated to reflux for 1 h. The reaction mixture is then cooled to ambient temperature and extracted with saturated aqueous sodium carbonate (15 ml) and water (2×5 ml). Final drying with magnesium sulphate and evaporation of the solvent and recrystallization from ethanol afforded the title compound as white crystals (78% yield), mp 236° C. MS: m/e=407(M+H$^+$).

EXAMPLE 2

(4-Methoxy-7-morpholin-4-yl-benzothiazol-2-yl)-carbamic acid phenyl ester (IV)

A suspension of 4-methoxy-7-morpholin-4-yl-benzothiazol-2-ylamine (26.5 g, 100 mmol) in dichloromethane (56 ml) and pyridine (56 ml, 700 mmol) is added phenyl chloroformate (15.7 ml, 125 mmol) at 0-5° C. and the reaction mixture is warmed to ambient temperature. After 1 h, water (7.2 ml, 400 mmol) was added and the reaction mixture is heated for 1 h to 45° C. Then ethyl acetate (250 ml) and 2M HCL (125 ml) were added and the organic phase separated. After removal of the solvent and recrystallization from tert.butyl-methyl ether and finally from ethanol the title compound was obtained as white solid (80% yield), mp 166-168° C. MS: m/e=386(M+H$^+$).

EXAMPLE 3

4-Methoxy-7-morpholin-4-yl-benzothiazol-2-yl-amine (II)

(2-Methoxy-5-morpholin-4-yl-phenyl)-thiourea (5.0 g, 19 mmol) in chloroform (130 ml) are treated with bromine (960 µl) and the mixture refluxed for 18 hours. After removal of the volatile components in vacuo, the product is recrystallized from THF (2.8 g, 57%). MS: m/e=266 (M$^+$).

EXAMPLE 4

(2-Methoxy-5-morpholin-4-yl-phenyl)-thiourea

Benzoyl-3-(2-methoxy-5-morpholin-4-yl-phenyl)-thiourea (8.0 g, 21 mmol), suspended in methanol (260 ml), are treated with 6 ml sodium methanolate (5.4M in methanol) and the mixture stirred until a white precipitate forms. The mixture is concentrated in vacuo, the crystals are isolated by filtration and washed with methanol and hexane (5.0 g 86%). MS: m/e=268 (M$^+$).

EXAMPLE 5

1-Benzoyl-3-(2-methoxy-5-morpholin-4-yl-phenyl)-thiourea

To a solution of 2-methoxy-5-morpholin-4-yl-phenylamine (4.6 g, 22 mmol) in acetone (140 ml) is added a solution of benzoyl isothiocyanate (3.4 ml, 25 mmol) in acetone (80 ml) and the reaction mixture is stirred for further 30 min at ambient temperature. After removal of the volatile components in vacuo, the product is isolated by flash chromatography (silica, eluent ethyl acetate/n-hexane 1:4, then 1:2) as a yellow solid (8.0 g, 97%). MS: m/e=272 (M$^+$).

EXAMPLE 6

2-Methoxy-5-morpholin-4-yl-phenylamine 4-(4-Methoxy-3-nitro-phenyl)-morpholine (6 g) is hydrogenated in dichloromethane (100 ml) and methanol (600 ml) using palladium on carbon (10%, 600 mg) for 12 hours. The catalyst is removed by filtration and the solution evaporated in vacuo. Purification by flash chromatography (silica, eluent ethyl acetate/n-hexane 1:1) affords the product as off-white solid (4.6 g, 88%). MS: m/e=209 (M+H$^+$).

EXAMPLE 7

4-(4-Methoxy-3-nitro-phenyl)-morpholine

4-Bromo-2-nitroanisol (8.5 g, 36 mmol), morpholine (3.8 ml, 44 mmol), potassium phosphate (11 g, 51 mmol), 2-biphenyl-dicyclohexyl phosphine (960 mg, 2.7 mmol) and palladium(II)acetate (411 mg, 1.8 mmol) are dissolved in dimethoxyethane (80 ml) and stirred at 80° C. for 96 hours. The mixture is then cooled to room temperature, diluted with ethyl acetate (50 ml) and filtrated through dicalite. Flash chromatography on silica (eluent dichloromethane/methanol 99:1) affords the product as red solid (6.0 g, 69%). MS: m/e=238 (M$^+$).

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. The compound of formula

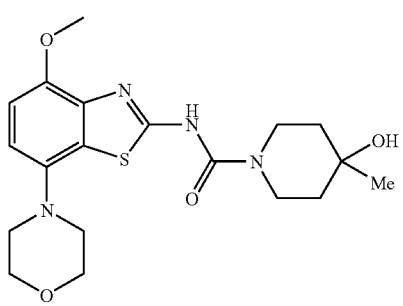

I which is 4-hydroxy-4-methyl-piperidine-1-carboxylic acid (4-methoxy-7-morpholin-4-yl-benzothiazol-2-yl)-amide, or a pharmaceutically acceptable acid addition salt thereof.

2. A pharmaceutical composition comprising a compound of formula I

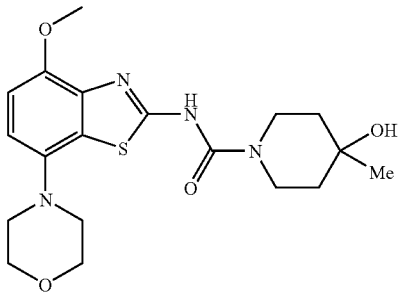

which is 4-hydroxy-4-methyl-piperidine-1-carboxylic acid (4-methoxy-7-morpholin-4-yl-benzothiazol-2-yl)-amide, or a pharmaceutically acceptable acid addition salt thereof, and a pharmaceutically acceptable excipient.

3. The pharmaceutical composition of claim 2, wherein the composition is in a form chosen from tablets, coated tablets, drages, hard gelatine capsules, soft gelatine capsules, solutions, emulsions, suspensions, suppositories, and injectable solutions.

4. The pharmaceutical composition of claim 2, wherein the pharmaceutically acceptable excipient is chosen from pharmaceutically inert, inorganic or organic carriers.

5. The pharmaceutical composition of claim 4, wherein the carrier is chosen from lactose, corn starch, talc, and stearic acids or its salts.

6. The pharmaceutical composition of claim 4, wherein the carrier is chosen from vegetable oils, waxes, fats, semi-solid polyols, and liquid polyols.

7. The pharmaceutical composition of claim 4, wherein the carrier is chosen from water, polyols, glycerol, and vegetable oil.

8. The pharmaceutical composition of claim 4, wherein the carrier is chosen from natural or hardened oils, waxes, fats, semi-liquid polyols, and liquid polyols.

9. The pharmaceutical composition of claim 4 further comprising one or more preservatives, solubilizers, stabilizers, wetting agents, emulsifiers, sweeteners, colorants, flavorants, salts for varying the osmotic pressure, buffers, masking agents and antioxidants.

* * * * *